United States Patent
Monros

(10) Patent No.: US 9,733,155 B2
(45) Date of Patent: Aug. 15, 2017

(54) ON-BOARD DIESEL EMISSIONS DIAGNOSTIC AND MONITORING SYSTEM

(71) Applicant: Serge V. Monros, Santa Ana, CA (US)

(72) Inventor: Serge V. Monros, Santa Ana, CA (US)

(*) Notice: Subject to any disclaimer, the term of this patent is extended or adjusted under 35 U.S.C. 154(b) by 0 days.

(21) Appl. No.: 14/820,332

(22) Filed: Aug. 6, 2015

(65) Prior Publication Data

US 2015/0346093 A1    Dec. 3, 2015

Related U.S. Application Data

(63) Continuation-in-part of application No. 14/168,982, filed on Jan. 30, 2014, now abandoned.

(60) Provisional application No. 61/759,456, filed on Feb. 1, 2013.

(51) Int. Cl.
| | |
|---|---|
| G01J 5/02 | (2006.01) |
| G01M 15/10 | (2006.01) |
| G01N 21/3504 | (2014.01) |
| G01N 21/39 | (2006.01) |
| G01J 3/42 | (2006.01) |
| G01J 5/00 | (2006.01) |

(52) U.S. Cl.
CPC ...... G01M 15/108 (2013.01); G01N 21/3504 (2013.01); G01N 21/39 (2013.01); G01J 3/42 (2013.01); G01J 5/0014 (2013.01); G01N 2021/399 (2013.01)

(58) Field of Classification Search
CPC ....... G01N 21/3504; G01J 3/42; G01J 5/0014
USPC ........................... 250/338.5, 339.13; 356/438
See application file for complete search history.

(56) References Cited

U.S. PATENT DOCUMENTS

| | | | | |
|---|---|---|---|---|
| 5,591,975 A | * | 1/1997 | Jack | G01N 21/3504 250/338.5 |
| 6,097,034 A | * | 8/2000 | Weckstrom | A61B 5/0836 250/343 |
| 6,271,522 B1 | * | 8/2001 | Lindermeir | G01N 21/255 250/338.5 |
| 6,603,555 B1 | * | 8/2003 | Nanami | G01N 21/39 356/236 |
| 7,176,460 B1 | * | 2/2007 | Wong | G01N 21/3504 250/336.1 |
| 2004/0052683 A1 | | 3/2004 | Fudali et al. | |
| 2004/0064243 A1 | | 4/2004 | Nakamura | |
| 2005/0092067 A1 | * | 5/2005 | Petrovic | G01N 21/0303 73/31.05 |
| 2006/0140713 A1 | | 6/2006 | Kobayashi | |
| 2009/0039284 A1 | * | 2/2009 | Goto | G01J 3/02 250/432 R |

(Continued)

*Primary Examiner* — Kenneth J Malkowski
(74) *Attorney, Agent, or Firm* — Kelly & Kelley, LLP

(57) ABSTRACT

In an apparatus and system for monitoring and communicating emissions data for a diesel engine, an exhaust gas analyzer uses laser light passed through a diffuser to measure the quantity of trace gases and particulates in an exhaust gas outlet from a diesel engine. The analysis chamber possesses superhydrophobic, superhydrophilic, and/or superoleophobic properties to reduce VOC-occlusion of the transparent chamber walls. A radio transmitter, cellular data transmitter, or Smartphone transmits measurement data. In a diagnostic and monitoring system for a diesel engine, the exhaust gas analyzer is in contact with the exhaust gases from the diesel engine, preferably in the tailpipe. A data receiver receives the transmitted measurement data.

16 Claims, 3 Drawing Sheets

(56) References Cited

U.S. PATENT DOCUMENTS

2011/0205535 A1* 8/2011 Soller ............... A61B 5/14552
356/300
2012/0311383 A1  12/2012 Sul et al.

* cited by examiner

ON-BOARD DIESEL EMISSIONS DIAGNOSTIC AND MONITORING SYSTEM

RELATED APPLICATION

This application is a continuation-in-part of U.S. patent application Ser. No. 14/168,982, filed on Jan. 30, 2014, which application claims the benefit of U.S. Provisional Application No. 61/759,456, filed on Feb. 1, 2013.

FIELD OF THE INVENTION

The present invention generally relates to diesel engine emissions. More particularly, the present invention relates to an apparatus and system for monitoring emissions from diesel engines.

BACKGROUND OF THE INVENTION

Diesel engines are widely used in a huge array of applications. Generally, diesel engines are classified as being either stationary or mobile. Stationary diesel engines include those used to generate power or compress air and other fluids. Hotels, casinos, and hospitals use large stationary diesel engines to generate power in the event of a power grid failure. Large industrial compressors are used in applications like construction, excavation and mining, or in mechanized assembly lines. Mobile diesel engines are even more ubiquitous. Mobile diesel engines can be found in: personal automobiles, commercial shipping trucks, aircraft, marine vessels (personal boats, commercial ships, tankers, tug boats, etc.), and locomotive engines used in rail transport. It is likely that an average person is affected, at least tangentially, by a diesel engine several times in any given day.

Diesel engines are extremely powerful, but they are also extremely dirty. Diesel engines run on diesel fuel, and diesel fuel emits a range of pollutants when it burns. Diesel fumes generally contain: carbon monoxide (CO), carbon dioxide ($CO_2$), nitrogen oxides (NOx), methane, and hydrocarbon particulates, among other pollutants. These gases and particulates are created as the diesel fuel burns, and are then expelled from the diesel engine as exhaust. Diesel exhaust is particularly problematic in that all the various gases contained therein cause an increase in the atmosphere's ability to trap infrared energy. This eventually creates holes in the ozone layer of the atmosphere and negatively effects global climates.

Diesel fumes cause another environmental problem called smog. Smog is a thick layer of pollution that can blanket entire geographical regions depending on the climate and weather patterns. Smog limits visibility (even on a clear day) and is very harmful if inhaled. When pollution is trapped in the atmosphere as described, it can also cause acid rain. Acid rain occurs when harmful pollutants dissolve into water droplets before they fall to the earth as rain. The resulting rain drops have a high pH level, which is why they are known as 'acid rain'. Acid rain damages crops and landscaping, and can even cause the paint on buildings, signs and cars to blister and peel. It has only been within the last few decades that the eye-opening effects of diesel engine fumes have been studied. Because of the detrimental nature of the pollution created by diesel engines, the government has stepped in to regulate the sources of diesel pollution.

The main governmental arm that deals with environmental regulations is the Environmental Protection Agency (EPA). The main function of the EPA is to write and enforce regulations based on the laws passed by Congress dealing with the environment. In the face of the environmental damage caused by diesel engine pollution, the EPA has enforced a whole host of regulations in an attempt to limit these harmful effects. The EPA currently regulates oil refinement, vehicle manufacturing, car sales across state borders, fuel sales, and almost every other aspect of fuel production and use. The EPA specifically regulates engine fuel systems and how much pollution any given engine can emit. With each passing year, these regulations become more and more strict. It is usually up to engine manufacturers to figure out how to stay in compliance with these emissions regulations. If the regulations are not met, engine manufacturers and users may be sanctioned.

One of the most logistically problematic areas of most EPA regulation schemes in this area is in monitoring engine emissions. For example, locomotive engines found in freight trains produce several thousand horsepower. Often, these engines are daisy-chained together in order to move tons of freight across the country. These engine use a large amount of fuel on initial start-up, so when they are awaiting assignment to the proper cargo, they are often left idling in train yards across the country. The EPA currently has regulations that seek to control the emissions of an idling locomotive, but these regulations simply state that an idling locomotive can emit no more than a given amount of particulates, $CO_2$, etc. per hour. No two engines, even of the same type, pollute at the same rate. Thus, train yards seeking to follow EPA regulations generally do not know which engines are the worst offenders and need to be shut off. As a result, a train yard operator may be forced to turn off every idling engine every 15 minutes or so in an attempt to ensure that the restricted level of emissions is not reached. But later, when the engine is turned on again, it uses more fuel on startup than it would have used had it been left idling. This means that the train yard is losing money. On the other side of the this problem, enforcement of the regulations on train yards not seeking to stay in line with the EPA mandate is almost logistically impossible. All the EPA can reasonably do is random inspections of idling locomotive engines in hopes of catching a polluter off-guard.

This same problem presents itself in several other venues as well. For example, trucking companies are subject to EPA regulations but truck engines may pollute differently depending on driving conditions (mountain roads, hot climates, high altitudes). So the trucking company may end up making expensive and unnecessary engine modifications in an attempt to satisfy EPA regulations. Conversely, the EPA has no effective way of monitoring emissions of truck engines while they are traveling from point A to point B. This same problem occurs with every other type of engine emission that the EPA seeks to regulate.

Accordingly, there is a need for a system and apparatus for monitoring diesel engine emissions in real time and presenting emissions data to engine owners or government regulators. The present invention fulfills these needs and provides other related advantages.

SUMMARY OF THE INVENTION

The present invention is directed to an exhaust gas analyzer comprising an analysis chamber having an exhaust intake and an exhaust outlet, the analysis chamber being transparent to light. A laser light source is disposed adjacent to the analysis chamber and a laser light detector is disposed adjacent to the analysis chamber generally opposite the laser light source. A laser light diffuser disposed between the laser light source and the analysis chamber. The laser light source and laser light detector are configured such that the laser light from the laser light source passing through the analysis chamber is received by the laser light detector. The laser light detector measures the amount of laser light energy passing through the analysis chamber. A logic processor is in electronic communication with the laser light detector and programmed to receive data of the measured laser light energy passing through the analysis chamber. A memory device is in electronic communication with the logic processor and configured to store the data of the measured laser light energy.

The logic processor is preferably configured to determine an amount of trace gases and particulates in exhaust gases passing through the analysis chamber based upon the amount of measured laser light energy. The data stored in the memory device represents the amount of trace gases and particulates in the exhaust gases passing through the analysis chamber.

A data output device is preferably included and in electronic communication with the memory device. The data output device may comprise a radio transmitter or a cellular data transmitter. The cellular data transmitter may comprise a Smartphone including a computer processor. The Smartphone may be in electronic communication with the laser light source, the laser light detector, and the logic processor and operates the exhaust gas analyzer or its components individually.

The exhaust gas analyzer preferably includes an external power supply or an internal battery electrically connected to the laser light source, the laser light detector, the logic processor and the memory device. The trace gases and particulates measured by the exhaust gas analyzer preferably include carbon monoxide, carbon dioxide, nitrous oxide, methane, and hydrocarbon particulates.

The surfaces of the analysis chamber that are exposed to exhaust gases preferably possess superhydrophobic properties, superhydrophilic properties, and/or superoleophobic properties.

A diagnostic and monitoring system for a diesel engine preferably comprises an exhaust gas analyzer as described above. The exhaust gas analyzer is in fluid communication with an exhaust gas outlet on the diesel engine. A data receiver is included and configured to receive measurement data from the exhaust gas analyzer.

The exhaust gas analyzer is preferably disposed in a tailpipe attached to the exhaust gas outlet such that exhaust gases from the diesel engine enter the exhaust intake on the exhaust gas analyzer. The exhaust gas analyzer is preferably electrically connected to a battery or an alternator associated with the diesel engine.

The data receiver is either a fixed device mounted proximate to the diesel engine or a handheld mobile device. The handheld mobile device is preferably configured to receive measurement data from exhaust gas analyzers in a plurality of diagnostic and monitoring systems for a plurality of diesel engines.

Other features and advantages of the present invention will become apparent from the following more detailed description, taken in conjunction with the accompanying drawings, which illustrate, by way of example, the principles of the invention.

BRIEF DESCRIPTION OF THE DRAWINGS

The accompanying drawings illustrate the invention. In such drawings.

DETAILED DESCRIPTION OF THE PREFERRED EMBODIMENTS

The present invention is a diagnostics system and apparatus for monitoring emissions from diesel engines. Specifically, the apparatus is a gas analyzer which is installed in a diesel engine at a location where it comes in contact with engine exhaust fumes. The gas analyzer reads the levels of different pollutants in the exhaust and is able to communicate this data in one of several ways, as will be described. The system of the current invention utilizes the pollutant readings from the engine to enable engine owners and environmental regulators to effectively marshal their resources in a timely and cost effective way. The diagnostics system for diesel engines of the present invention is generally referred to in the illustrations by the number 10.

Figure 1:
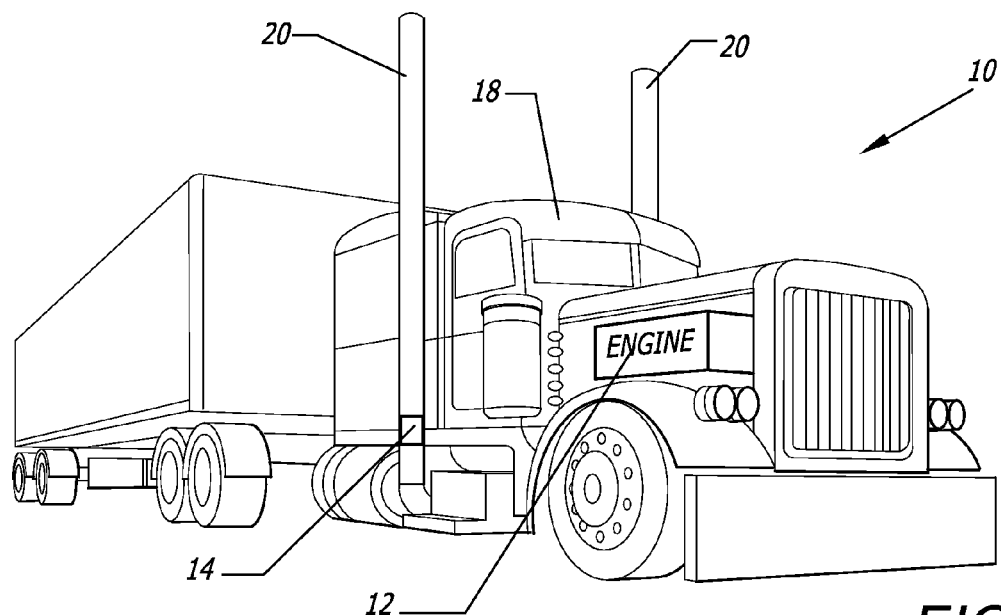
FIG. 1 is a perspective view of a truck with a diesel engine and the present invention installed in the smoke stack.

In FIG. 1, the diagnostics system 10 is illustrated as installed in a large diesel truck 18. The engine 12 of the truck 18 runs on diesel fuel and produces exhaust that exits the engine through the exhaust pipes 20. The engine exhaust of a diesel engine is very dirty and contains pollutants and noxious gases as described above. A gas analyzer 14 is placed in the exhaust pipes 20 of the engine 12 such that the analyzer 14 comes in direct contact with the exhaust fumes produced by the engine 12. In this way, the analyzer 14 can give accurate readings for the pollutants contained within the exhaust.

Figure 2:
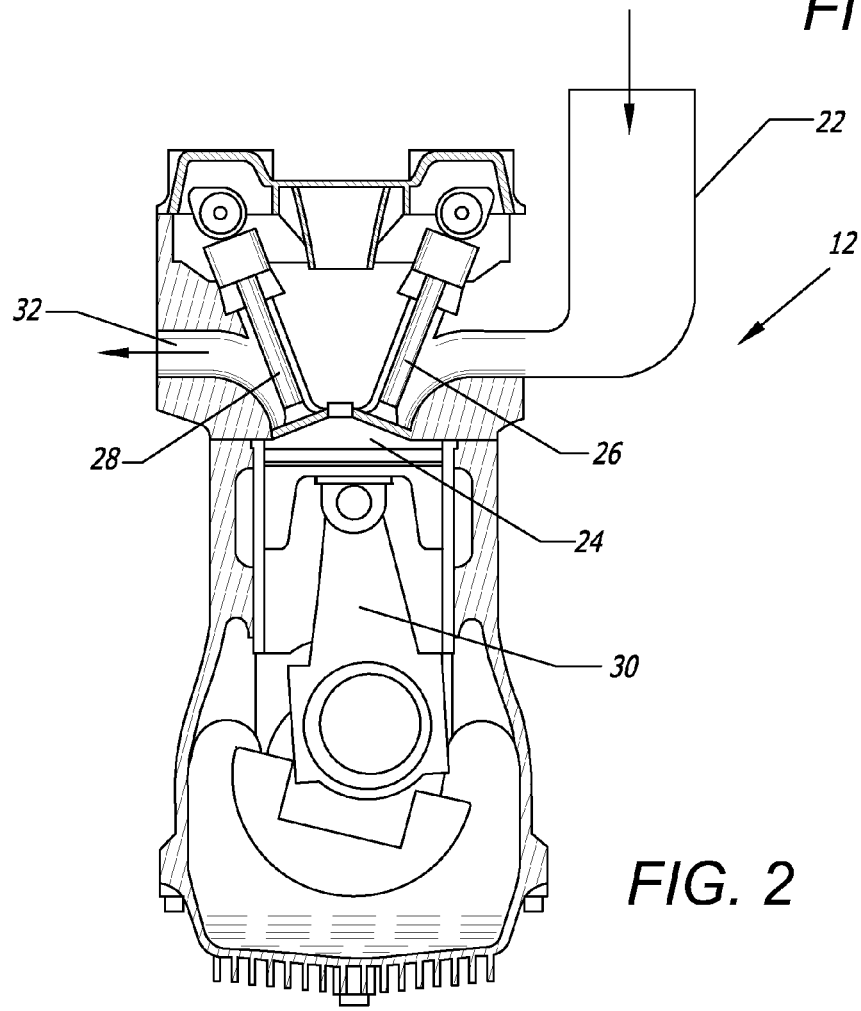
FIG. 2 is a cross-sectional view of a diesel engine illustrating the various stages of the combustion cycle along with the intake and exhaust flows.

The combustion cycle that produces exhaust fumes is illustrated in the cross-sectional view of an engine 12 in FIG. 2. The process starts with the engine intake 22. Here, fuel and air are mixed and fed into the engine 12. The fuel/air mixture is fed past the intake valve 26 into the combustion chamber 24. At this point the intake valve 26 seals the combustion chamber 24 and the piston 30 moves upward creating a tremendous amount of pressure in the combustion chamber 24. When the pressure in the combustion chamber 24 is sufficient, the fuel/air mixture combusts, creating an explosion that forces the piston 30 away from the combustion chamber 24. At this point, the exhaust valve 28 opens to evacuate any unburned fuel through the engine exhaust port 32. The combustion of the diesel fuel in the combustion chamber 24 is not perfect. This means that there is often unburned fuel left behind. Additionally, diesel fuel is not a very efficient fuel, so rather than burning completely upon ignition, it leaves behind many polluting by-products. All of this is evacuated out of the engine exhaust at this point in the cycle. It is this exhaust that the diagnostics system 10 seeks to analyze and monitor.

Figure 3:
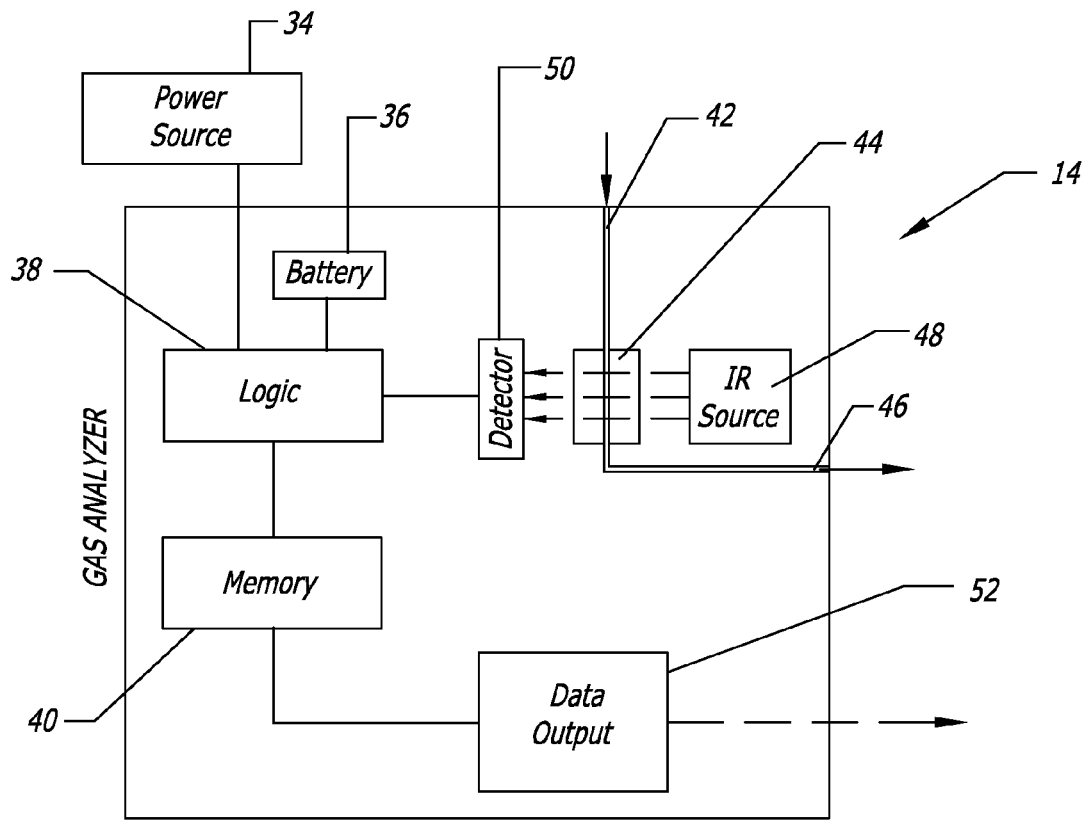
FIG. 3 is a schematic diagram of the infrared gas analyzer of the present invention illustrating the data path and logic.

The diagnostics system 10 includes a gas analyzer 14, 14' that is placed in an engine 12 such that it comes in direct contact with the exhaust produced by that engine 12. The gas analyzer 14 is illustrated in a schematic diagram in FIG. 3. In one preferred embodiment, the gas analyzer 14 is a standard five gas analyzer with specific modifications. A five gas analyzer measures trace amounts of various gases by determining the absorption of an emitted infrared light source through a certain air sample. In FIG. 3, the gas analyzer 14 has an infrared source 48 that passes infrared energy through an analysis chamber 44. The infrared energy is received by a detector 50 directly opposite. The detector 50 reads the amount of infrared energy that passes through the exhaust sample in the analysis chamber 44 and determines the amount of trace gases that reside in the exhaust sample. The exhaust sample enters the analysis chamber 44 via an exhaust intake 42. Once analysis is complete, the exhaust sample is pushed out the exhaust evacuation port 46.

The gas analyzer 14 is small and can run off a battery 36 or a constant power source 34 outside the gas analyzer 14. This outside power source 34 could be the engine battery. The gas analyzer 14 is capable of detecting trace amounts of the following: CO, CO2, NOx, Methane, and hydrocarbon particulates. Prior art gas analyzers typically feature an analog or digital readout that allows an operator to read the results of the analysis.

Figure 5:
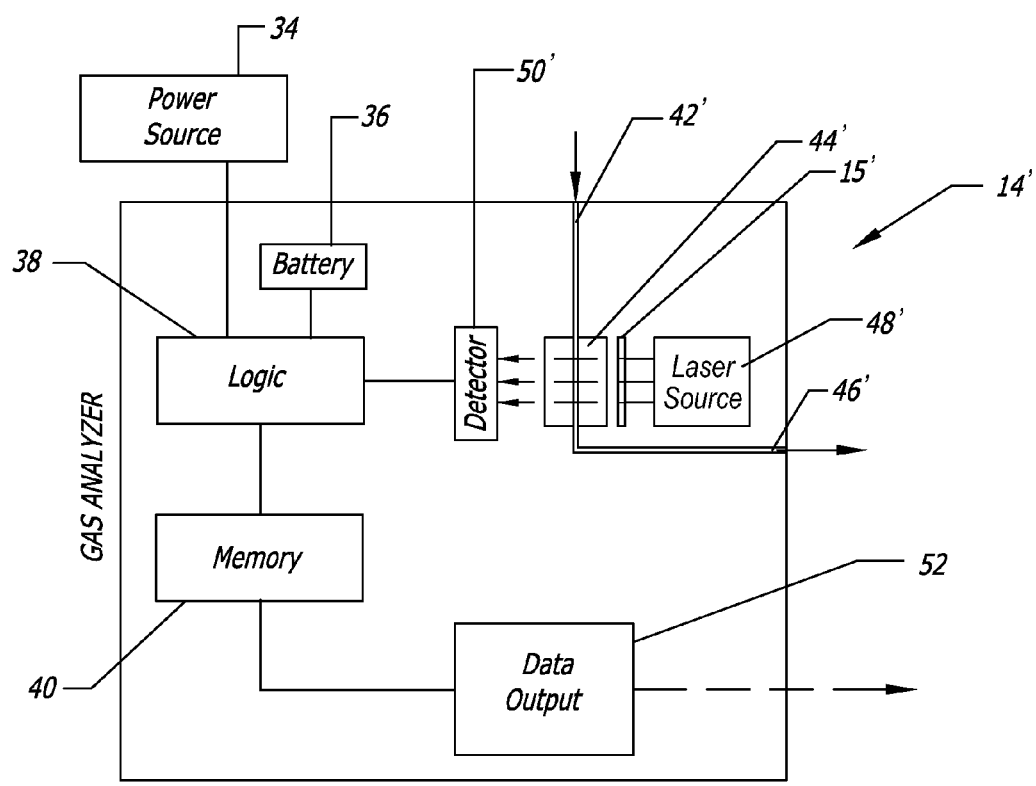
FIG. 5 is a schematic diagram of an alternate embodiment utilizing a laser light gas analyzer.

In a second preferred embodiment, as shown schematically in FIG. 5, the gas analyzer 14' may comprise a laser/diffuser system as opposed to the infrared energy system described above. The infrared energy system suffers from several drawbacks, including that such infrared applications are near-ubiquitous in automotive engine systems, and that infrared light is non-specific to particulate types. In contrast, a laser-based system can be tuned to detect specific kinds, types, sizes, etc. of particulates found in exhaust gases. A laser/diffuser gas analyzer 14' provides for more reliable detection of the variety of constituent components typically found in the exhaust gases. The gas analyzer 14' may specifically include tunable diode laser spectroscopy technology that use a suite of different light sources and detectors across a broad range of light energy frequencies, including visible, non-visible, infrared, ultraviolet, and other frequencies.

As a specific example, with infrared systems, it is not possible to characterize diameters of particulates. When diesel engines lose compression or ignition efficiency, the nature of the particulates is increased, both in terms of quantity and in diameters. A laser gas analyzer 14' would enable the system to detect increased quantities and diameters as a specific detection function. The laser gas analyzer 14' could then report these increased quantities and diameters as an indicator that the diesel engine is losing compression.

The laser gas analyzer 14' is preferably coupled with a light diffuser 15 configured to smooth and homogenize the laser light to eliminate hot spots and uneven light distribution. The diffuser 15 may also be used to shape the laser light as in a specific cone angle—either symmetrical or elliptical—depending upon the designed detection field of the laser gas analyzer 14'. Such diffusers 15 combined with laser gas analyzers 14' may be used to detect and characterize the nature and composition of exhaust gases in real-time using simple emitter-detector circuits based on tuned laser-diffuser calibrations. Such laser gas analyzers 14' paired with diffusers 15 provide a simplified on-board exhaust gas analyzer built right into the exhaust system of an engine 12.

In FIG. 5, the gas analyzer 14' has a laser source 48' that passes laser light energy through an analysis chamber 44'. While the analysis chamber 44' is depicted as an exhaust by-pass having an intake 42' and an evacuation port 46', the analysis chamber 44' of this particular embodiment of gas analyzer 14' may exist in the primary exhaust source or outlet on the engine 12. The laser light energy passes through the diffuser 15 before entering the analysis chamber 44' and intersecting the exhaust gases. The analysis chamber 14' is transparent to the laser light energy generated by the source 48' and shaped by the diffuser 15. After passing through the analysis chamber 44', the laser light energy is received by a laser light detector 50' directly opposite the source 48'. The detector 50' reads the quantity and quality of laser light energy that passes through the exhaust gases in the analysis chamber 44' and determines the amount of trace gases that reside in the exhaust gases.

As with the first embodiment, the gas analyzer 14' may run off a battery 36 or a constant power source 34 outside the gas analyzer 14'. This outside power source 34 could be the engine battery. The gas analyzer 14' is capable of detecting trace amounts of the following: CO, CO2, NOx, Methane, and hydrocarbon particulates.

In whichever form, the gas analyzer 14, 14' is preferably modified in order to be able to store and communicate the results of the gas analysis. As such, the gas analyzer 14, 14' has computer logic 38 that is powered by either the battery 36 or the external power source 34. The computer logic 38 receives the results of the exhaust gas analysis from the detector 50. The computer logic 38 can determine whether preset limits have been reached or exceeded and can also send the results of the exhaust analysis to the computer memory 40. The computer memory 40 may be long-term memory or short-term memory or a combination of both. Once the results and analysis have been stored, they are broadcast via the data output 52. The data output 52 of the gas analyzer 14, 14' varies in two embodiments as discussed below.

Figure 4:
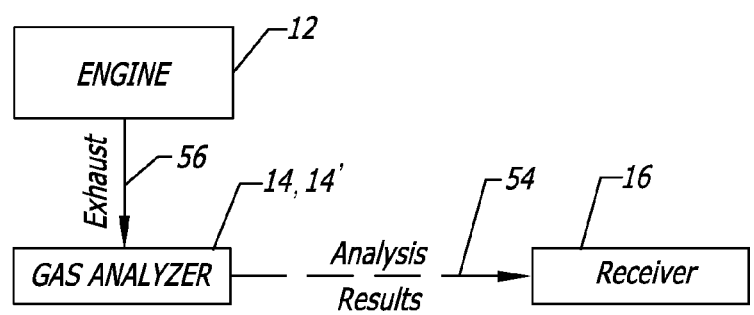
FIG. 4 is a schematic diagram of the present invention illustrating how the receiver interacts with the gas analyzer.

In the first embodiment, the gas analyzer 14, 14' is configured to include computer logic 38 and memory 40 for storing and communicating the analysis results, as described above. In this first embodiment, the data output 52 is a radio transmitter. The radio transmitter continuously broadcasts the gas analysis results. The radio signal can be picked up by a handheld receiver outside the engine (see FIG. 4). This embodiment is useful if, for example, a train yard owner wishes to take readings from all the engines currently operating in the train yard. He only has to walk around the yard with the hand-held receiver and take readings from the analyzers currently installed. If the radio transmitters in the gas analyzers are strong enough, the train yard owner may be able to take emissions readings without leaving the main office of the yard. This embodiment is also useful for government regulators making surprise inspections. The regulator only has to stand near the engine being inspected. The gas analyzer 14, 14' and transmitter of this embodiment are small enough to fit within the exhaust pipe 20 of an engine 12 and are preferably powered by the engine battery (not shown). A supplemental on-board back up battery 36 may also be provided within the gas analyzer 14, 14'.

The second embodiment is more sophisticated than the first and includes a gas analyzer 14, 14' where the data output 52 is a specially programmed Smartphone. A Smartphone is a mobile phone built on a mobile operating system. This device has more computing capability and connectivity than a standard phone. It basically combines a personal computer with a telephone. Smartphone's typically feature relatively fast microprocessors, memory storage, Wi-Fi and data network connectivity, Global Positioning Satellite (GPS) navigation, and a high resolution display. The Smartphone is connected to the gas analyzer 14, 14' such that the smartphone can operate the analyzer and store the analysis results. In this embodiment of the gas analyzer 14, 14', the power source 34 is preferably the engine battery, but the gas analyzer 14, 14' may also include an on-board back up battery 36.

The programmable smartphone enables this embodiment of the gas analyzer 14, 14' to be utilized at virtually any distance. For example, a shipping company with a fleet of 800 trucks can install this embodiment of the gas analyzer 14, 14' into each truck. From the shipping company's headquarters, emissions data can be gathered from any truck at any time. The analyzer's Smartphone may be programmed to only answer calls from the shipping company's headquarters. Once the call is connected an analysis computer at the shipping company's headquarters pulls all the emissions data stored on the Smartphone. Alternately, the Smartphone can be pre-programmed to activate the gas analyzer, collect an emissions sample and call the company headquarters with the results. This can happen at any time interval desired. The Smartphone attached to the gas analyzer may also be equipped with a Global Positioning Satellite (GPS) locator. This means that along with being able to collect emissions data from any engine at any time, the shipping company can also know the exact location of every truck in their fleet at any time.

One challenge found with the use of light or laser emitter detector systems such as the gas analyzers 14, 14' described above is occlusion of the detector surface when exposed to exhaust gases. When a detector surface, such as the analysis chamber 44 described above, is exposed to particulates such as those found in diesel engine exhaust gases, the surface through which the light or laser source passes through can become occluded with volatile organic compound (VOC) particulates. Such VOC particulates very easily adhere to the surface of most emitter-detector arrays. Once such surfaces become clouded by surface contamination, the gas analyzer 14, 14' would become useless.

To address this type of VOC-occlusion, the gas analyzers 14, 14' of the present invention preferably use self-cleaning surfaces having features such as superhydrophobicity, superhydrophilicity, or superoleophobicity. The feature of superhydrophobicity may be achieved by the application of an appropriate material or film to the analysis chamber 44, 44', such as a blend of a silicone resin and a fluorocarbon as described in U.S. Patent Application Publication No. 2006/0085921. In the context of this invention, superhydrophobicity refers to surfaces in which the contact angle of a water droplet exceeds 150 degrees with a roll-off angle/contact angle by hysteresis of less than 10 degrees. Such superhydrophobicity helps to reduce VOC-occlusion by repelling water droplets and other materials that may be present in the water droplets so as to prevent the water droplets from drying on the surface and leaving the other materials behind with resulting VOC-occlusion.

Alternatively, the feature of superhydrophilicity may be achieved by the application of an appropriate material or film, such as a transparent ceramic consisting of alumina, magnesium aluminate spinel, yttria alumina garnet (YAG), neodymium-doped Nd:YAG, or other similar compounds. In the context of this invention, superhydrophilicity refers to surfaces on which water droplets form substantially no contact angle, e.g., almost zero degrees. Such superhydrophobic materials help to reduce VOC-occlusion by taking on water more readily, which helps to dissolve build-up and wash off the same. The superhydrophobic and superhydrophilic properties may be realized on the same surface by application of precise two-dimensional micropatterns. The superhydrophobic and superhydrophilic materials may also comprise the analysis chamber 44, 44' themselves so as to remove the need to apply a coating.

Alternatively, the analysis chamber 44, 44' may consist of superoleophobic materials. In the context of this invention, superoleophobic refers to surfaces that basically repel oil-based materials of the type that may be present in exhaust gases and cause build-up on the surface of the analysis chamber 44, 44'. Through the use of such superoleophobic materials, including, for example, a fluoroalkyl-functional precipitated silica and a fluoropolymer binder, or fluoroalkylsilane-treated precipitated silica aggregates, the surface of the analysis chamber 44, 44' may remain clean and clear of VOC-occlusion or be more easily cleaned of such VOC materials.

Government regulators may use the programmable smartphone of the second embodiment to great advantage. For example, a law may be passed requiring all shipping fleets to install gas analyzers in a certain percentage of their engines. Regulators would then be able to view emissions data at any time from any shipping company. Emissions data could be collected automatically, or could be requested on a case by case basis. The programmable smart phone in the gas analyzer 14, 14' distributed by the regulators may optionally be included with a connection to the internal engine startup mechanism (not shown). Then for example, if the engine is polluting above a given level after repeated warnings, the engine may be shut down remotely by the regulators. This system would provide government regulators with the ability to test engine owners for emissions compliance easily at any time. This could also provide the EPA and other regulators with a vehicle to generate a substantial amount of residual income from fees/fines. Monies generated by this process could be managed by a phone company who administers the cellular phone lines utilized by the smart phone in the gas analyzer 14, 14'. Alternately, monies may be managed by a third party.

The system of the present invention is collecting emissions data from diesel engines, as described above and illustrated in FIG. 4. Here, an overview is illustrated wherein an engine 12 creates exhaust 56 which is then analyzed by a gas analyzer 14, 14'. The analysis results 54 are broadcast to a receiver 16, as in one of the embodiments described above. This system also provides engine owners with a unique opportunity for monetizing the cleanliness of their engines. The United States has a program that allows over-polluters to buy "carbon credits" from under-polluters. A carbon credit is equivalent to a certain amount of pollution over a given time. The EPA assigns carbon credits to companies based on the type of industry the company is in. It is possible for a company to under-pollute; that is, to produce less pollution than their assigned amount of carbon credits allows them to pollute. This carbon credit surplus can be very valuable to another company that produces more pollution than their allotment of carbon credits allows for. With the system of the present invention in place, and under-polluter will be able to more accurately determine at any time exactly how much pollution it is producing and exactly how much carbon credit surplus it has or needs.

Although several embodiments have been described in detail for purposes of illustration, various modifications may be made to each without departing from the scope and spirit of the invention. Accordingly, the invention is not to be limited, except as by the appended claims.

What is claimed is:

1. A diagnostic and monitoring system for a diesel engine, comprising:

an exhaust gas analyzer in fluid communication with an exhaust gas outlet on the diesel engine, wherein the exhaust gas analyzer comprises an analysis chamber containing a portion of exhaust gas from the diesel engine, the analysis chamber being transparent to light, a laser light source disposed adjacent to the analysis chamber, a laser light diffuser disposed between the laser light source and the analysis chamber, a laser light detector disposed adjacent to the analysis chamber and generally opposite the light source, such that light from the laser light source passing through the analysis chamber is received by the laser light detector, wherein the laser light detector measures laser light energy passing through the analysis chamber, a logic processor in electronic communication with the laser light detector, the logic processor programmed to receive data of the measured laser light energy passing through the analysis chamber, and a memory device in electronic communication with the logic processor, the memory device configured to store the data of the measured laser light energy;

wherein the logic processor is configured to detect increased particulate quantities and diameters in the exhaust gas based upon the measured laser light energy, and determine whether the diesel engine has lost compression or ignition efficiency;

wherein the memory device is configured to store a detected increase in particulate quantities and diameters in the exhaust gas and a determination that the diesel engine has lost compression or ignition efficiency; and a data receiver configured to receive measurement data from the exhaust gas analyzer.

2. The diagnostic and monitoring system of claim 1, wherein the exhaust gas analyzer is disposed in a tailpipe attached to the exhaust gas outlet, such that exhaust gases from the diesel engine enter an exhaust intake on the analysis chamber of the exhaust gas analyzer.

3. The diagnostic and monitoring system of claim 1, wherein the data receiver is a fixed device mounted proximate to the diesel engine or a hand-held mobile device.

4. The diagnostic and monitoring system of claim 3, wherein the hand-held mobile device is configured to receive measurement data from exhaust gas analyzers in a plurality of diagnostic and monitoring systems for a plurality of diesel engines.

5. The diagnostic and monitoring system of claim 1, wherein the exhaust gas analyzer is electrically connected to a battery or an alternator associated with the diesel engine.

6. The diagnostic and monitoring system of claim 1, wherein the logic processor is configured to determine an amount of trace gases and particulates in exhaust gases passing through the analysis chamber based upon the measured laser light energy.

7. The diagnostic and monitoring system of claim 6, wherein the data stored in the memory device represents the amount of trace gases and particulates in the exhaust gases passing through the analysis chamber.

8. The diagnostic and monitoring system of claim 1, further comprising a data output device in electronic communication with the memory device.

9. The diagnostic and monitoring system of claim 8, wherein the data output device comprises a radio transmitter or a cellular data transmitter.

10. The diagnostic and monitoring system of claim 9, wherein the cellular data transmitter comprises a Smartphone, including a computer processor.

11. The diagnostic and monitoring system of claim 10, wherein the Smartphone is in electronic communication with the laser light source, the laser light detector, and the logic processor, wherein the Smartphone operates the exhaust gas analyzer.

12. The diagnostic and monitoring system of claim 1, further comprising an external power supply or an internal battery electrically connected to the laser light source, the laser light detector, the logic processor and the memory device.

13. The diagnostic and monitoring system of claim 6, wherein the trace gases and particulates comprise carbon monoxide, carbon dioxide, nitrous oxide, methane, and hydrocarbon particulates.

14. The diagnostic and monitoring system of claim 1, wherein surfaces within the analysis chamber that are exposed to exhaust gases possess superhydrophobic properties.

15. The diagnostic and monitoring system of claim 1, wherein surfaces within the analysis chamber that are exposed to exhaust gases possess superhydrophilic properties.

16. The diagnostic and monitoring system of claim 1, wherein surfaces within the analysis chamber that are exposed to exhaust gases possess superoleophobic properties.

* * * * *